United States Patent
Brull et al.

(10) Patent No.: US 9,603,858 B2
(45) Date of Patent: Mar. 28, 2017

(54) COMPOSITIONS FOR PREVENTING AND TREATING AN IMMUNE SYSTEM DISORDER

(75) Inventors: Florence Brull, Maashricht (FI);
Ronald P. Mensink, Echt (FI);
Jogehum Plat, Gealle (FI)

(73) Assignee: RAISIO NUTRITION LTD., Raisio (FI)

(*) Notice: Subject to any disclaimer, the term of this patent is extended or adjusted under 35 U.S.C. 154(b) by 0 days.

(21) Appl. No.: 13/253,835

(22) Filed: Oct. 5, 2011

(65) Prior Publication Data

US 2012/0135956 A1  May 31, 2012

Related U.S. Application Data (63) Continuation-in-part of application No. 12/955,551, filed on Nov. 29, 2010, now abandoned.

(51) Int. Cl.
| | | |
|---|---|---|
| *A61K 31/575* | (2006.01) | |
| *A61K 31/716* | (2006.01) | |
| *A23L 33/105* | (2016.01) | |

(52) U.S. Cl.
CPC ......... *A61K 31/575* (2013.01); *A23L 33/105* (2016.08); *A61K 31/716* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 5,502,045 A | 3/1996 | Miettinen et al. | |
| 6,063,776 A * | 5/2000 | Ostlund, Jr. | 514/182 |
| 6,129,944 A | 10/2000 | Tiainen et al. | |
| 6,174,560 B1 | 1/2001 | Miettenen et al. | |
| 6,190,720 B1 | 2/2001 | Yuan et al. | |
| 7,285,297 B1 * | 10/2007 | Waggle et al. | 424/757 |
| 2005/0182037 A1 | 8/2005 | Fergusson et al. | |
| 2012/0135970 A1* | 5/2012 | Brull et al. | 514/170 |

FOREIGN PATENT DOCUMENTS

| | | |
|---|---|---|
| EP | 1142494 A1 | 10/2001 |
| WO | WO 98/58554 | 12/1998 |

(Continued)

OTHER PUBLICATIONS

Bateman et al. Global guidelines: a global strategy for asthma management and prevention: GINA executive summary. Eur. Respir. J. 2008; 143-178.*

(Continued)

*Primary Examiner* — Anna Pagonakis
(74) *Attorney, Agent, or Firm* — Arent Fox LLP (57) ABSTRACT

The present invention relates to methods of treating, preventing, or decreasing the occurrence of a condition characterized by Th2 overactivation or impaired Th1, or mitigating symptoms associated with a condition characterized by Th2 overactivation or impaired Th1, comprising orally administering to a subject in need thereof an effective amount of a composition comprising a plant stanol and/or plant stanol ester. The present invention also relates to methods of improving the health status of a subject suffering from asthma and increasing the levels of IL-10 in a subject in need thereof.

12 Claims, 3 Drawing Sheets a  $p < 0.05$ vs cholesterol
b  $p < 0.10$ vs cholesterol
c  $p < 0.10$ vs control cholesterol    sitostanol (56) References Cited

FOREIGN PATENT DOCUMENTS

| WO | WO 02/12348 A2 | | 2/2002 |
|----|----|----|----|
| WO | WO 02/065859 | * | 8/2002 |
| WO | WO 2008/102151 A1 | | 8/2008 |
| WO | WO 2009/147297 A2 | | 12/2009 |

OTHER PUBLICATIONS

Daughtery. T lymphocytes in atherosclerosis: the ying-yang of Th1 and Th2 influence on lesion formation. Cir. Res. 2002; 90: 1039-1040.*
Oh et al. Comparison of microvessel density before and after peripheral blood stem cell transplantation in multiple myeloma patients and its clinical implications: multicenter trial. International Journal of Hematology, 76, 465-470, 2002.*
Ostlund. Phytosterols in Human Nutrition. Annu. Rev. Nutr. 2002. 22: 533-49.*
Kate Blease et al., "Therapeutic Effect of IL-13 Immunoneutralization During Chronic Experimental Fungal Asthma," The Journal of Immunology, 166, pp. 5219-5224 (2001).
P.A. Eigenmann et al., "Avirulant *Salmonella typhimurium* strains prevent food allergy in mice," Clinical and Experimental Immunology, 151, pp. 546-553 (2008).
Christophe P. Frossard et al., "Oral administration of an IL-10-secreting Lactococcus lactis strain prevents food-induced IgE sensitization," J Allergy Clinical Immunology, vol. 119, No. 4, pp. 952-959 (2007).
Ulrike Breytenbach et al., "Flow Cytometric Analysis of the Th1-Th2 Balance in Healthy Individuals and Patients Infected with the Human Immunodeficiency Virus (HIV) Receiving a Plant Sterol/Sterolin Mixture," Cell Biology International 2001, vol. 25, No. 1, pp. 43-49 (2001).
Laura Calpe-Berdiel et al., "Dietary phytosterols modulate T-helper immune response but do not induce apparent anti-inflammatory effects in a mouse model of acute, aseptic inflammation," Life Science 80, 1951-6 (2007).
Anne O'Garra et al., "Twenty-first Century Foxp3," Nature Immunology, vol. 4, No. 4, pp. 304-3066 (2003).
Rebecca C. Taylor et al., "Toll-like receptor 2 ligands inhibit $T_H2$ responses to mite allergen," J Allergy Clinical Immunology, vol. 117, No. 5, pp. 1148-1154 (2006).
Kristen Page et al., "A TLR2 Agonist in German Cockroach Frass Activates MMP-9 Release and is Protective against Allergic Inflammation in Mice," The Journal of Immunology, 183, pp. 3400-3408 (2009).

* cited by examiner

Figure 3

COMPOSITIONS FOR PREVENTING AND TREATING AN IMMUNE SYSTEM DISORDER

CROSS-REFERENCE TO RELATED APPLICATION

This application is a Continuation-In-Part of U.S. patent application Ser. No. 12/955,551, filed Nov. 29, 2010, the entire specification claims and drawings of which are incorporated herewith by reference.

FIELD OF INVENTION

The present invention relates to the field of health. Especially it concerns compositions for oral use suitable for preventing or mitigating asthma symptoms.

BACKGROUND OF THE INVENTION

Food products enriched with components having cholesterol lowering effect beyond normal nutrition have been commercially available for some time. Representative examples are food products enriched with plant stanol or sterol fatty acid esters.

U.S. Pat. No. 5,502,045 discloses plant stanol fatty acid esters and the cholesterol lowering effects thereof as well as a suitable method for their preparation. Dietary intake of 2 to 3 g/day of plant stanols is reported to lower serum LDL cholesterol levels in man up to 14% without affecting HDL cholesterol levels. The amount of atherogenic apolipoprotein B particles in blood is also decreased, thus reducing the risk of CVD.

Current research literature and especially FDA's approval of a health claim for plant stanols and plant sterols have increased the interest of the food industry in supplementing foods with plant stanols and plant sterols. Indeed, many such food items have been introduced into the market. It is assumed that new plant stanol and plant sterol containing foods will appear into the market rapidly.

U.S. Patent Application Publication No. 2005/0182037 discloses a composition for treating or preventing an immune system disease, such as colds, flu, diabetes, allergies, asthma, pneumonia, fibromyalgia, HIV infection, hepatitis C infection, multiple sclerosis, fibromyalgia and rheumatoid arthritis. The composition comprises phytosterols, essential fatty acid complexes and antioxidants which components are claimed to have a synergistic effect. As phytosterols are mentioned β-sitosterol, stigmasterol, campesterol, brassicasterol and their associated glucosides. The essential fatty acid complexes facilitate the body's absorption of β-sitosterol. To have an effect on immune system diseases the phytosterols therefore seem to need to be absorbed effectively.

All references cited herein are hereby incorporated by reference in their entirety.

SUMMARY OF THE INVENTION

The present invention includes a method of treating, preventing, or decreasing the occurrence of a condition characterized by Th2 overactivation or impaired Th1, or mitigating symptoms associated with a condition characterized by Th2 overactivation or impaired Th1, comprising orally administering to a subject in need thereof an effective amount of a composition comprising a plant stanol and/or plant stanol ester The present invention also includes a method of improving the health status of a subject suffering from asthma, the method comprising administering orally an effective amount of plant stanol and/or plant stanol ester to the subject in need thereof.

The present invention also includes a method of treating, preventing, or decreasing the occurrence of asthma, or mitigating the symptoms of asthma of a subject, the method comprising administering orally an effective amount of plant stanol and/or plant stanol ester to the subject in need thereof.

The present invention also includes a method of increasing the level of interleukin-10 in the blood of a subject in need thereof by administering orally an effective amount of plant stanol and/or plant stanol ester to the subject.

The present invention also relates to a method for reducing the amount and/or severity of asthmatic exacerbations and/or asthma attacks in an asthma patient comprising administering orally a composition comprising an effective amount of plant stanol and/or plant stanol ester to the patient in need thereof.

According to the present invention it was surprisingly found that although plant stanols are very poorly absorbed, they were able to alter the Th1/Th2 balance into a more Th1 dominant immune response. Th1 stands for Type 1 helper T and Th2 for Type 2 helper T.

This discovery suggests that the plant stanols and/or plant stanol esters can be consumed by subjects suffering from a disease caused by a Th2 dominant immune response, especially asthma. By asthma is here meant conventional asthma i.e. allergic asthma.

DETAILED DESCRIPTION OF THE INVENTION

In one aspect of the present invention there is provided a composition comprising a plant stanol and/or a plant stanol ester for use in treatment, prevention, or decrease in the occurrence of conditions characterized by Th2 overactivation or impaired Th1 response. The compositions of the present invention may also be administered to mitigate symptoms associated with a condition characterized by Th2 overactivation or impaired Th1 response.

In another aspect of the present invention, the compositions comprising a plant stanol and/or a plant stanol ester may be administered to increase the levels of interleukin-10 in the blood of a subject in need thereof. The levels may be increased to levels which are normal and found in healthy subjects, or the levels may be increased to a level wherein the subject experiences an improvement in i.e. alleviation of symptoms associated with low interleukin-10 levels.

It has now surprisingly been shown that the plant stanol and/or plant stanol ester has the effect of altering the Th1/Th2 balance into a more dominant Th1 direction. By a "dominant" Th1 direction is not necessary meant that it is more active than Th2, but describes the direction of the alteration towards a more active Th1 than without treatment with plant stanol and/or plant stanol ester.

Surprisingly the plant stanol and/or plant stanol ester increases the concentrations of Th1 specific cytokines which are INFγ (γ-interferon) and IL-2 (interleukin-2), and/or inhibits the activity of Th2 cells by the cytokine IL-10.

The condition caused by Th2 overactivation can be asthma. It is known asthma patients therefore have a low concentration of IL-10 as compared to healthy persons; healthy persons meaning persons without asthma or related immune system diseases.

The plant stanol is preferably sitostanol or campestanol or a mixture thereof. Preferably the plant stanol comprises at least 50% by weight sitostanol, typically from 55 to 90% by weight sitostanol. The amount of campestanol is typically from 10 to 45% by weight of the plant stanol. In addition there may be a small amount of minor components (non-sterol unsaponifiable components), preferably less than 5% by weight, more preferably less than 3% by weight, and most preferably less than 1% by weight.

The plant stanol may also be used in the form of a plant stanol ester. The plant stanol ester is preferably sitostanol ester or campestanol ester or a mixture thereof. Preferably the plant stanol part of the plant stanol ester comprises at least 50% by weight sitostanol, typically from 55 to 90% by weight sitostanol. The amount of campestanol is typically from 10 to 45% by weight of the plant stanol part. In addition there may be a small amount of minor components (non-sterol unsaponifiable components), preferably less than 5% by weight, more preferably less than 3% by weight, and most preferably less than 1% by weight.

The ester is preferably formed with a fatty acid as will be described below. The stanol fatty acid ester is most preferably as disclosed in U.S. Pat. No. 6,174,560, included herewith by reference.

The composition of the present invention may in addition to plant stanol and/or plant stanol ester comprise a plant sterol and/or a plant sterol ester. Preferred plant sterols are sitosterol, campesterol, stigmasterol and brassicasterol and mixtures thereof. Correspondingly preferred plant sterol esters are sitosterol, campesterol, stigmasterol and brassicasterol ester and mixtures thereof. The ester is preferably formed with a fatty acid as will be described below.

In the composition of the present invention the molar ratio of the sum of plant stanol and plant stanol ester to the sum of plant sterol and plant sterol ester is preferably at least 1:1, more preferably at least 2:1, still more preferably at least 4:1 and most preferably at least 9:1.

In the composition of the present invention the molar ratio of the sum of plant stanol and plant stanol ester to the sum of plant sterol and plant sterol ester is preferably from 99.9:0.1 to 50:50, more preferably from 99.9:0.1 to 60:40, and most preferably from 99.9:0.1 to 70:30.

The composition of the present invention may additionally comprise β-glucan. Useful β-glucans are described in e.g. WO 02/12348 and WO 2008/102151 included herewith by reference. The preferred β-glucan comprise beta-(1,3)-glycosidic linkages and optionally further beta-(1,6)-linkages. These glucans can be obtained from yeast or fungi. A most preferred β-glucan is a glucan having a beta-(1,3)-backbone with one or more beta-(1,3)-side chains linked thereto which structure preferably may be altered as compared to its naturally occurring structure. Such glucans have been suggested for use in the treatment of asthma and related diseases of abnormal pulmonary function in an animal.

The β-glucan comprising beta-(1,3)-glycosidic linkages, and optionally further beta-(1,6)-linkages, will have an improved i.e. a more pronounced reducing effect on asthma symptoms. There will probably be such a synergistic effect between the plant stanol/plant stanol ester and the β-glucan.

According to an embodiment of the invention the composition is in the form of a food product comprising at least one nutritional ingredient in addition to the plant stanol and/or plant stanol ester and the optional components plant sterol and/or plant sterol ester, and/or β-glucan. The term nutritional ingredient includes components containing energy such as fat, carbohydrates and/or proteins.

The food product may be in the form of a product selected from the group consisting of bakery, confectionery, cereal, snacks, beverage, dairy, dairy substitute, sauce, soup, meat, fish, poultry, vegetable oil based and ready mix products.

The amount of the plant stanol and/or plant stanol ester and, if present, the plant sterol and/or plant sterol ester in the food product, calculated as sterol equivalents, is from 0.05 to 20 g per 100 g food product. Preferably this amount is from 0.1 to 20 g, more preferably from 0.2 to 15 g and most preferably from 0.5 to 15 g per 100 g food product. Thus, this amount means the sum of plant stanol and optional plant sterol in free or esterified form.

Preferably the amount of the plant stanol and/or plant stanol ester calculated as sterol equivalents, is from 0.05 to 20 g per 100 g food product. More preferably this amount is from 0.1 to 20 g, still more preferably from 0.2 to 15 g and most preferably from 0.5 to 15 g per 100 g food product. Thus, this amount means the total amount of plant stanols in free or esterified form.

According to another embodiment of the invention the composition is in the form of a dietary supplement comprising the plant stanol and/or plant stanol ester, and the optional components a) plant sterol and/or plant sterol ester, and/or b) β-glucan.

The dietary supplement may be in the form of a capsule, tablet, granule, powder, syrup, dispersion or suspension. It is aimed to be swallowed directly or to be added into or on a meal.

The amount of the plant stanol and/or plant stanol ester and, if present, the plant sterol and/or plant sterol ester in the food product or dietary supplement is such that the active ingredient(s) is consumed/administered at a rate of at least 0.4 g per day, typically a rate of 0.4 to 20 g, preferably 0.5 to 20 g, and more preferably 0.8 to 5 g per day calculated as sterol equivalents.

Preferably the amount of the plant stanol and/or plant stanol ester in the food product and in the dietary supplement is such that the plant stanol/plant stanol ester is consumed/administered at a rate of at least 0.2 g per day, typically a rate of 0.2 to 20 g, preferably 0.4 to 20 g, more preferably 0.5 to 20 g, and most preferably 0.8 to 5 g per day calculated as sterol equivalents.

The composition of the present invention may further comprise additional components such as emulsifiers.

According to a second aspect of the invention there is provided a method for the treatment or prevention of conditions characterized by Th2 overactivation or impaired Th1 response in a subject, comprising orally administering to the subject a composition comprising a plant stanol and/or plant stanol ester, in an amount effective for treating or preventing the condition.

By "oral administration" or "oral use" of the composition is in this specification meant ingesting the composition, i.e. swallowing the composition as such or after chewing or crunching it in the mouth in order for the composition to be delivered into the digestive tract (intestine). The time the composition is delayed in the mouth is therefore typically from 0.5 to 30 seconds, more typically from 0.5 to 15 seconds. Practically this means eating or drinking the composition, especially if the composition is a food product.

By effective amount or sufficient amount is here meant the amount of plant stanol and/or plant stanol ester needed to show an effect on at least one of the clinical measurements disclosed herein (IL-10, IL-2, INF-γ) in vivo in a subject in need of a treatment of asthma. Alternatively, the effective amount can be recognized by noticing a reduction of symptoms of asthma in a subject suffering from this disease. Typical amounts are the daily doses mentioned here above.

The composition of the present invention besides having the known properties of improving the overall serum total lipid profile, for instance in reducing blood serum total and/or LDL cholesterol levels, the composition additionally is useful in the treatment of asthma or related diseases.

As used here, the term "plant stanol" refers to any stanol as defined in the following and having the ability to alter the Th1/Th2 balance into a more Th1 dominant immune response.

Plant stanols in esterified form may be formed e.g. with fatty acids (2-24 carbon atoms, more typically 16-22 carbon atoms, saturated, monounsaturated or polyunsaturated, including also special fatty acids such as conjugated fatty acids, e.g. CLA, EPA and DHA), hydroxybenzoic acids or hydroxycinnamic acids (ferrulic or coumaric acids) or other organic acids such as e.g. di- or tricarboxylic acids and/or hydroxy acids or with any combination of the said acids. Most preferred are the plant stanol fatty acid esters. Plant sterols in esterified form may be formed correspondingly. In addition, any combinations of the free and various esterified forms are also included.

As used here, the term "plant stanol in esterified form" or "plant stanol ester" refers to plant stanols having at least 60%, preferably at least 85%, most preferably at least 95% of the plant stanols in esterified form. Correspondingly, the term "plant sterol in esterified form" or "plant sterol ester" refers to plant sterols having at least 60%, preferably at least 85%, most preferably at least 95% of the plant sterols in esterified form.

In this specification the stanols include 4-desmethyl stanols and the sterols include 4-desmethyl sterols. Typical 4-desmethyl stanols are sitostanol and campestanol. Typical 4-desmethyl sterols are sitosterol, campesterol, stigmasterol, brassicasterol, 22-dehydrobrassicasterol, and 55-avenasterol.

In this specification the amounts of plant stanols and plant sterols and their esters are calculated as plant "sterol equivalents" i.e. as the total amount of free plant stanol and optional free plant sterol, excluding the possible acid parts of the ester molecules.

Commercially available plant stanols in their free or esterified form can be used as such. When plant stanols in their free form are used, the particle size of the plant stanols is preferably small enough to enhance the dispersability, dissolvability and solubility of the plant stanols. Particle size reduction can be accomplished by many techniques known in the art, e.g. by different dry or wet grinding or micromilling techniques described for example in U.S. Pat. No. 6,129,944, WO 98/58554 and EP 1142494. Other components, such as a suitable admixture can be pulverized together with plant stanols, the choice of the other components depending on the food material or dietary supplement in which the active ingredients are to be added. Examples of the admixture include various structure and flavor enhancers, as well as flours especially in case the active ingredients are to be added into bakery products. The above applies to plant sterols as well.

Plant stanols/plant sterols in their free form may also be used molten to prepare a food product, dietary supplement, or an ingredient to be included in such products, especially in compositions containing an emulsifier and/or a fat. Preferably a homogenous mixture that is easily used in the compositions of the present invention is formed from plant stanols/plant sterols and an emulsifier and/or a fat by heating plant stanols to their melting point, to 60-150° C., typically to 130-150° C., and adding the emulsifier and/or fat to the stanols/sterols, either prior to or after heating. Suitable techniques that can be utilized are described e.g. in U.S. Pat. No. 6,190,720. Most preferably a blend of plant stanols/plant sterols and emulsifier(s) and/or fat is heated until the components are dissolved. The mixture is cooled under agitation prior to adding it into the compositions of the present invention.

Preferably the plant stanol/plant sterol in esterified form is a plant stanol fatty acid ester/plant sterol fatty acid ester. The fatty acid ester is technically very suitable for incorporation into a wide range of different products and is especially preferred as it has very good organoleptic properties, enabling production of the compositions of the present invention with good organoleptic properties.

In the following some typical compositions of the present invention and the preparation thereof will be explained in more detail.

The plant stanol or plant stanol ester may be added into food products or dietary supplements separately as an ingredient. The active ingredient is added into food material or dietary supplements by conventional processes for producing these products.

Commercially available plant stanols in free form can be used as such, or more preferably the particle size of the plant stanols is reduced to enhance the dispersability and solubility of plant stanols as described above. Molten plant stanols in free form can also be used to prepare food products, dietary supplements, or ingredients for preparing these. Advantageously the main part of plant stanols in esterified form is melted, if needed, before addition into food products or dietary supplements. Also powders containing plant stanol ester can be used as e.g. disclosed in WO2009/147297, included herewith by reference.

The food product of the present invention can be in the form of various food compositions, including but not restricted to bakery products and confectionery (fresh and dry bakery products, e.g. fresh bread, other bread products, cakes, muffins, waffles, biscuits, crackers etc.)

cereal products and snacks (breakfast cereals, muesli, bars, such as cereal based and muesli bars, such bars possibly containing chocolate, pasta products, flours etc.)

beverages (alcoholic and non-alcoholic drinks, including e.g. soft drinks, juices and juice-type mixed drinks, fortified beverages such as protein or calcium fortified beverages, probiotic drinks, sport and energy drinks, meal replacement drinks, concentrates or premixes for beverages and powdered drinks where the content of compositions of the present invention is calculated for the ready-to-use form)

dairy products (milk, milk based products, e.g. cheese, cream cheese and the like, yoghurt, frozen yoghurt, other frozen dairy foods, drinkable yoghurt, other fermented milk products, dairy beverages, ice cream, desserts, spreads etc.)

dairy substitutes (i.e. non-dairy products such as soy, oat or rice based dairy substitutes e.g. imitations of milk, cheese, yoghurt, ice cream)

sauces, soups meat, fish, poultry products (e.g. sausages, meat balls)

vegetable oil based products (margarines, spreads, dressings, mayonnaise etc.)

ready mixes (for baking e.g. breads, cakes, muffins, waffles, pizzas, pancakes; or for cooking e.g. soups, sauces, desserts, puddings) to be used in preparing or manufacturing foods.

The food product of the present invention can also contain other nutritionally beneficial components, some of which may further enhance the effects of the compositions of the present invention. The food can be fortified with these components or the components can be an intrinsic part of the other food ingredients.

Examples of the nutritionally beneficial components include n-3 fatty acids, e.g. from fish oil or certain vegetable oils such as rapeseed, flaxseed and camelina oil; dietary fibre; diacylglycerol; and beneficial minor components, for example isoflavones, tocopherols, tocotrienols, carotenoids, vitamin C, folate and flavonoids. Also other vitamins and minerals (e.g. K, Mg, Ca) may be added or included in the food products of the present invention. Any of the nutritionally beneficial components may also be included in the dietary supplement disclosed herein.

In a further aspect of the present invention there is provided a dietary supplement for treating or preventing asthma comprising a composition of the present invention as defined above. Said product can additionally contain at least one compounding agent. The compounding agent can be any pharmaceutically acceptable binder, carrier, diluent, excipient or coating agent. The product can be in any suitable form, e.g. tablets, granules, powders, capsules, syrups, dispersions or other liquid preparations for oral administration.

The compositions according to the present invention are most preferably incorporated into food products, and especially into food products designed for being part of a healthy diet.

The invention is also related to a method for improving the health status of a subject suffering from asthma. In the method plant stanol and/or plant stanol ester is administered orally to a subject in need thereof in an effective amount. This amount should be sufficient to increase the blood concentration of at least one of the cytokines selected from IFNγ, IL-2 and IL-10, preferably of IL-10. The increase is typically at least 10%, more typically at least 50%, still more typically at least 100%, and most typically at least 200% compared to a control blood sample of the subject without prior ingestion of any plant stanol and plant stanol ester. Preferably the subject is ingesting a normal diet without any addition of plant sterol or plant sterol ester prior to the time of taking the control blood sample. Typically this amount of plant stanol and/or plant stanol ester may be at least 0.2 g per day calculate as sterol equivalents. Other typical amounts and compositions, which can be used in this method are disclosed above. The improvement in health status may also be verified directly by evaluating the prevention or mitigation of asthma symptoms of the subject upon administration of the plant stanol and/or plant stanol ester.

The invention is further related to a method of reducing the risk to become diseased with asthma in a subject in need thereof. In the method plant stanol and/or plant stanol ester is administered orally in a effective amount. This amount should be sufficient to increase the concentration of at least one of the cytokines selected from IFNγ, IL-2 and IL-10, preferably of IL-10. Typically this amount may be at least 0.2 g per day calculated as sterol equivalents. Other typical amounts and compositions, which can be used in this method are disclosed above.

The invention is further related to a method of preventing or mitigating (alleviation of) the symptoms of asthma in a subject in need thereof. In the method plant stanol and/or plant stanol ester is administered orally in a sufficient amount to obtain at least a reduction of the asthma symptoms. This amount should be sufficient to increase the concentration of at least one of the cytokines selected from IFNγ, IL-2 and IL-10, preferably of IL-10. The increase is typically at least 10%, more typically at least 50%, still more typically at least 100%, and most typically at least 200% compared to a control blood sample of the subject without prior ingestion of any plant stanol and plant stanol ester. Preferably the subject is ingesting a normal diet without any addition of plant sterol or plant sterol ester, as well as no addition of plant stanol or plant stanol ester as already mentioned above, prior to the time of taking the control blood sample. Typically a sufficient amount of plant stanol and/or plant stanol ester is at least 0.2 g per day calculated as sterol equivalents. Other typical amounts and compositions, which can be used in this method are disclosed above. The prevention or mitigation of the symptoms of asthma of a subject may of course also directly be evaluated in this method.

The invention is also related to a method for improving the health status of a subject suffering from asthma. The method comprises the subject ingesting a sufficient amount of a food product as disclosed above.

The invention also preferably relates to a method of preventing or mitigating (alleviation of) the symptoms of asthma in a subject in need thereof. The method comprises the subject ingesting a sufficient amount of a food product as disclosed above.

The invention is also related to a method for reducing the amount (recurrence) and/or severity of asthmatic exacerbations (asthmatic paroxysms or asthma attacks) in an asthma patient. The method comprises administering orally a composition comprising an effective amount of plant stanol and/or plant stanol ester, preferably included in a food product, to the patient in need thereof.

The invention is also related to a method of increasing the level of interleukin-10 in the blood of a subject in need thereof by administering orally a sufficient amount of plant stanol and/or plant stanol ester to the subject. The compositions, especially food products, usable for this are as disclosed above. Also the size of the increase in the IL-10 level is as disclosed above. Increasing the IL-10 level in a subject with asthma symptoms is a potential method for prevention or mitigation of asthma symptoms.

The invention is further illustrated by the following examples.

Example 1

Asthma is characterized by a Th2 (T-helper cell subtype 2) dominant immune response i.e. increased production of Th2 cytokines IL-4 and IL-13 by Peripheral Blood Mononuclear Cells (PBMCs). No differences in Th1 (T-helper cell subtype 1) cytokine production (such as IFNγ and IL-2) are found when asthma patients are compared to healthy controls.

Another T-helper cell subtype that is characterized by the production of IL-10, are the regulatory T-cells. Their main function is to inhibit the activity of either the Th1 or the Th2 cells, in order to prevent overactivity of one of these subtypes.

In mice, IL-13 is shown to be causally related to the prevalence of asthmatic symptoms, as all symptoms disappeared after blocking the IL-13 receptor (1). Again in mice, Eisenmann et al. (2) have shown that stimulation of Th1 cells has a protective effect against allergic reactions.

They evaluated the effects of micro-organisms such as Salmonella typhimurium, which induce a Th1 response, administered to C3H/HeOuJ female mice in the presence of an allergy inducing antigen. Mice treated with the micro-organisms were protected against an allergic response. This approach has, however, not been carried out with plant sterols or plant stanols, but is illustrative for the strength of Th1 activation in the control of hypersensitivity reactions. From the same group, Frossard et al. (3) showed that increasing serum IL-10 concentrations lowered the allergic response in antigen-triggered mice. This suggests that modulating the activity of these regulatory T-cells can play an important role in inhibiting hyperresponsive reactions as seen in allergies, characterized by Th2 overactivation, in vivo.

The aim of this study was to determine whether plant stanols, despite limited absorption, induce a shift towards a more Th1 dominant immune response in ex vivo stimulated PBMCs from asthma patients.

Test Persons and Protocol 20 people were enrolled in the study: 10 asthma patients and 10 healthy controls. Healthy controls were matched to the asthma patients in sex, age and body mass index (BMI). The subject characteristics are shown in Table 1. Exclusion criteria were smoking, diabetes, autoimmune diseases, inflammatory diseases, and the use of plant stanol or plant sterol enriched food products. Blood was taken twice from each participant, with a four-week interval. Peripheral blood mononuclear cells (PBMCs) were isolated and cultured with either cholesterol or sitostanol added to the culture. The concentration of PBMCs in the test culture was the same as in blood naturally. The concentrations of sitostanol and cholesterol were 1.2 µM. After 52 hours of stimulation with PHA (phytohemagglutinin), cytokine concentrations in the culture medium were determined. Cholesterol was added as a control to see whether the observed effects were specific plant stanol effects.

TABLE 1

Subject characteristics
Data are presented as mean ± sd and there are no significant differences between the groups.

|  | Healthy controls | Asthma patients |
|---|---|---|
| M/F | 3/7 | 3/7 |
| Age | 32 ± 10 | 32 ± 10 |
| BMI | 25.4 ± 2.9 | 25.7 ± 2.9 |
| Cholesterol | 5.6 ± 0.99 | 5.8 ± 0.89 |
| LDL-C | 3.4 ± 1.00 | 3.5 ± 0.67 |
| HDL-C | 1.5 ± 0.36 | 1.7 ± 0.49 |
| Triglycerides | 1.5 ± 0.49 | 1.4 ± 0.60 |

Results

Figure 1:
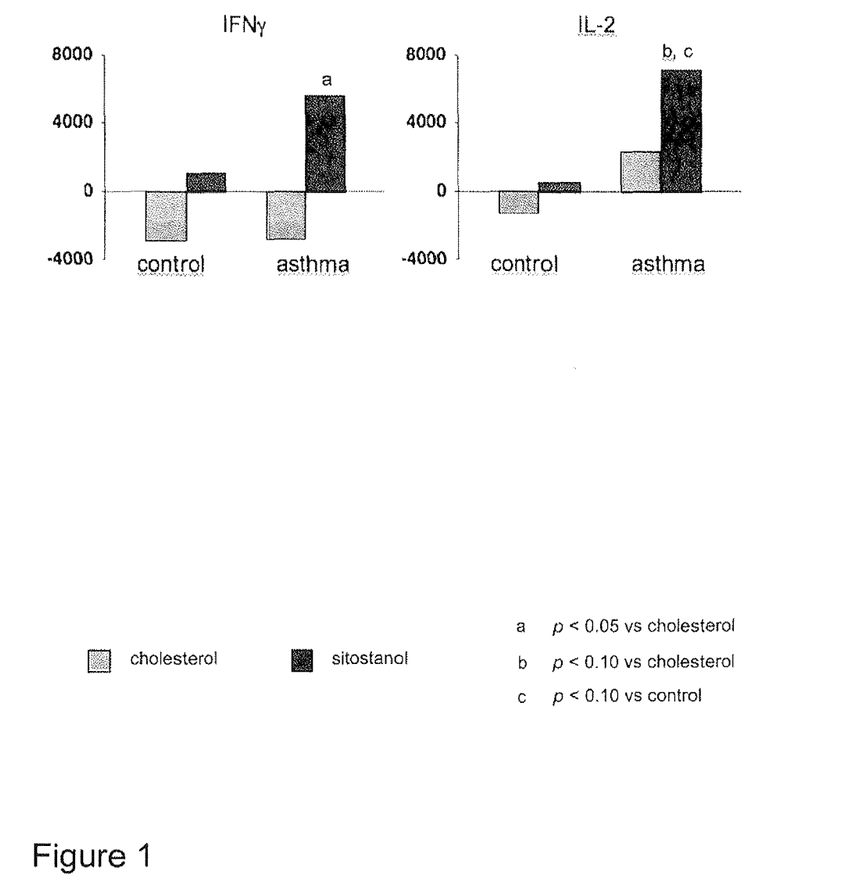
FIG. 1 shows experimental results of the effect of plant stanol on the Th1 specific cytokines IL-2 and IFNγ.

FIG. 1 shows that sitostanol increases concentrations of Th1 specific cytokines (IL-2 and IFNγ) in the culture medium. Data are presented as changes in pg/ml vs. the control condition (PHA stimulated PBMCs).

As shown in FIG. 1, sitostanol increased the production of Th1 cytokines IFNγ and IL-2.

Figure 2:
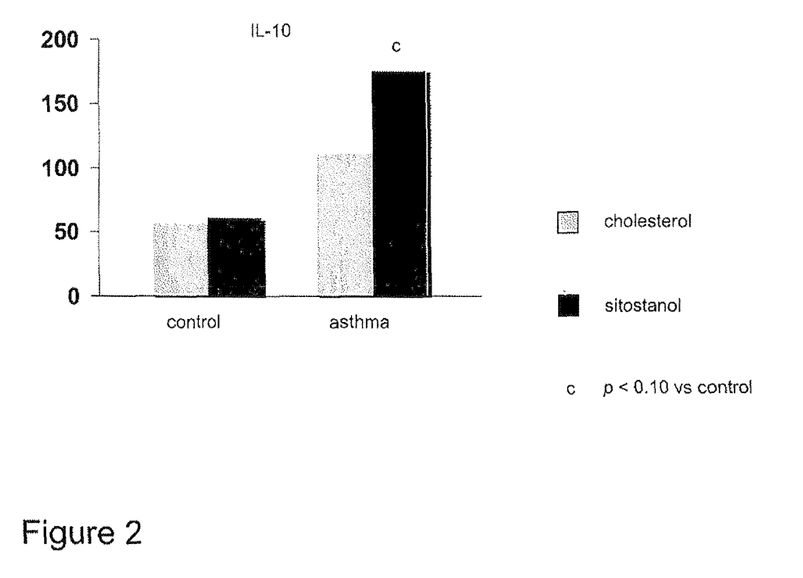
FIG. 2 shows experimental results of the effect of plant stanol on the production of Treg cytokine IL-10.

FIG. 2 shows that sitostanol induces IL-10 production in PBMCs from asthma patients. Data are presented as changes in pg/ml vs. control condition (PHA stimulated PBMCs).

Also the production of Treg cytokine IL-10 increased in the PBMCs of asthma patients when compared to the control condition (FIG. 2).

Discussion and Conclusion

Literature suggests that plant sterols are able to increase the activity of Th1 cells (4, 5). It was now surprisingly found that sitostanol, although absorbed at a much lower level, induces a Th1 response in PBMCs, particularly from asthma patients. This knowledge may be exploited to induce beneficial effects on the disturbed—Th2 dominant—immune response of these patients. Also the increase in Treg cytokine IL-10 might fit this paradigm, as this cytokine is able to inhibit the activity of Th2 cells, when their response is dominant (6).

From a mechanistic perspective, we found that sitostanol induces this Th1 shift via activation of TLR2. It is known that TLR2 activation has positive effects on asthma. More into detail, adding a TLR2 agonist to cells challenged with a house dust mite extract, which induces an allergic response (i.e. an increase in IL-13 production), significantly reduced the production of IL-13 (7). Moreover, Page et al. (8) have shown that the allergic response to a cockroach extract is significantly higher in TLR2(−/−) mice than in TLR(+/+) wild type mice, also suggesting a protective effect of TLR2 on allergic responses. Altogether, stimulating TLR2 seems promising in relation to health improvement in asthma patients. Also increasing the amount of IL-10 in the blood of asthma patients seems to improve the patients' health status.

Conclusions

Plant stanol induces an ex vivo Th1 shift in isolated and PHA stimulated PBMCs from asthma patients. This stimulating effect of plant stanol on Th1 seems promising in relation to health improvement in asthma patients.

Plant stanol accomplishes to increase the level of IL-10 in isolated and PHA stimulated PBMCs from asthma patients. This increase seems promising in relation to health improvement in asthma patients.

Example 2

The aim of this study is to test the immune response in asthma patients eating plant stanol ester compared to patients not eating it.

58 patients with clinically proven asthma were included in the double-blind randomized placebo-controlled study. The subjects kept their dietary habits the same during the entire study, as well as the level of physical exercise and smoking habits. They were not allowed to use cox-2 inhibitors (e.g. naproxen and ibuprofen) as that could have had an immune modulating effect. The subjects continued their habitual asthma-medication use. The use of prednisone, which inhibits T-helper cell activity, was however an exclusion criterion in the study. The subjects consumed control soyghurts (without plant stanol ester) in an amount of a cup of 150 ml soy-based yoghurt/day for a run-in period of two weeks. After this an eight-week intervention period started in which 29 subjects consumed plant stanol ester enriched soyghurt (4 g plant stanol/day) and the other 29 subjects continued eating the control soyghurts. At week four of the intervention period, all subjects were vaccinated against Hepatitis A Virus (HAVRIX 1440, GlaxoSmithKline, containing inactivated viral particles). The subjects were not allowed to have had a previous vaccination against hepatitis A, to ensure that the initial response of the immune system, without the interference of memory cells, was measured. After this, antibody titres against Hepatitis A Virus (a mixture of IgM and IgG) were measured weekly up to four weeks after vaccination. The antibody titres were measured using ELISA kits (Enzygnost, Siemens Diagnostics). The mean antibody titres as a function of time are given in FIG. 3.

Figure 3:
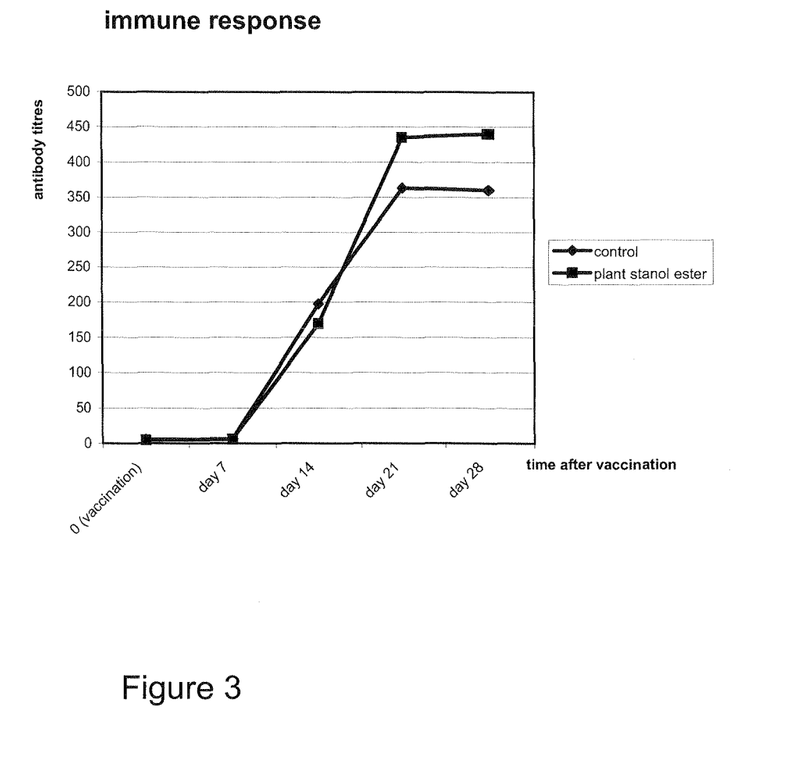
FIG. 3 shows experimental results of the effect of plant stanol ester in asthma patients on the immune response after vaccination measured as antibody titers as a function of time after the vaccination.

As can be seen from FIG. 3, the plant stanol ester group obtained a stronger immune response compared to the control group. The difference was statistically significant at weeks 7 (day 21 in the figure) and 8 (day 28 in the figure) of the intervention. Therefore, plant stanol ester improved immune function also in vivo in asthma patients. This, on the other hand, is an implication that the amount and severity of asthmatic exacerbations will be reduced in asthma patients.

REFERENCES

1 Blease, K, C Jakubzick, J Westwick, N Lukacs, S L Kunkel, C M Hogaboam: Therapeutic effect of IL-13 immunoneutralization during chronic experimental fungal asthma. *J Immunol* 166, 5219-24 (2001).
2 Eigenmann, P A, K E Asigbetse, C P Frossard: Avirulant Salmonella typhimurium strains prevent food allergy in mice. *Clin Exp Immunol* 151, 546-53 (2008).
3 Frossard, C P, L Steidler, P A Eigenmann: Oral administration of an IL-10-secreting *Lactococcus lactis* strain prevents food-induced IgE sensitization. *J Allergy Clin Immunol* 119, 952-9 (2007).
4 Breytenbach, U, A Clark, J Lamprecht, P Bouic: Flow cytometric analysis of the Th1-Th2 balance in healthy individuals and patients infected with the human immunodeficiency virus (HIV) receiving a plant sterol/sterolin mixture. *Cell Biol Int* 25, 43-9 (2001).
5 Calpe-Berdiel, L, J C Escola-Gil, S Benitez et al.: Dietary phytosterols modulate T-helper immune response but do not induce apparent anti-inflammatory effects in a mouse model of acute, aseptic inflammation. *Life Sci* 80, 1951-6 (2007).
6 O'Garra, A, P Vieira: Twenty-first century Foxp3. *Nat Immunol* 4, 304-6 (2003).
7 Taylor, R C, P Richmond, J W Upham: Toll-like receptor 2 ligands inhibit Th2 responses to mite allergen. *J Allergy Clin Immunol* 117, 1148-54 (2006).
8 Page, K, J R Ledford, P Zhou, M Wills-Karp: A TLR2 agonist in German cockroach frass activates MMP-9 release and is protective against allergic inflammation in mice. *J Immunol* 183, 3400-08 (2009).

The invention claimed is:

1. A method of treating asthma comprising orally administering to a subject in need thereof an effective amount of a composition comprising a sitostanol fatty acid ester, wherein the fatty acid has 2-24 carbon atoms.

2. The method according to claim 1, wherein the composition additionally comprises a glucan comprising beta-(1, 3)-glycosidic linkages.

3. The method according to claim 1, wherein the composition is a food product.

4. The method according to claim 3, wherein the food product is selected from the group consisting of bakery, confectionery, cereal, snacks, beverage, dairy, dairy substitute, sauce, soup, meat, fish, poultry, vegetable oil based and ready mix products.

5. The method according to claim 1, wherein the composition is a dietary supplement.

6. The method according to claim 5, wherein the dietary supplement is administered in the form of a capsule, tablet, granule, powder, syrup, dispersion or suspension.

7. A method for treating an asthma patient, comprising administering orally a composition comprising an effective amount of a sitostanol fatty acid ester to the patient in need thereof, wherein the fatty acid has 2-24 carbon atoms.

8. The method according to claim 7, wherein the composition additionally comprises a glucan comprising beta-(1, 3)-glycosidic linkages.

9. The method according to claim 7, wherein the composition is a food product.

10. The method according to claim 9, wherein the food product is selected from the group consisting of bakery, confectionery, cereal, snacks, beverage, dairy, dairy substitute, sauce, soup, meat, fish, poultry, vegetable oil based and ready mix products.

11. The method according to claim 7, wherein the composition is a dietary supplement.

12. The method according to claim 11, wherein the dietary supplement is administered in the form of a capsule, tablet, granule, powder, syrup, dispersion or suspension.

* * * * *